United States Patent
Guittet et al.

(10) Patent No.: US 7,577,280 B2
(45) Date of Patent: Aug. 18, 2009

(54) MEASUREMENT OF MITOTIC ACTIVITY

(75) Inventors: Christelle Marie Guittet, Malvern (GB); Paul Gerard Ducksbury, Malvern (GB); Maria Petrou, Guildford (GB); Anastasios Kesidis, Athens (GR); Roberto Cipolla, Cambridge (GB); Margaret Jai Varga, Malvern (GB)

(73) Assignee: Qinetiq Limited (GB)

( * ) Notice: Subject to any disclaimer, the term of this patent is extended or adjusted under 35 U.S.C. 154(b) by 607 days.

(21) Appl. No.: 10/535,140

(22) PCT Filed: Nov. 13, 2003

(86) PCT No.: PCT/GB03/04916

§ 371 (c)(1), (2), (4) Date: May 17, 2005

(87) PCT Pub. No.: WO2004/047004

PCT Pub. Date: Jun. 3, 2004

(65) Prior Publication Data

US 2006/0098858 A1    May 11, 2006

(30) Foreign Application Priority Data

Nov. 18, 2002  (GB)  .................................. 0226787.0

(51) Int. Cl.
*G06K 9/00* (2006.01)
*C07H 21/02* (2006.01)
(52) U.S. Cl. ........................ 382/128; 382/165; 536/23.1
(58) Field of Classification Search ................ 382/100, 382/128, 129, 130, 131, 132, 133, 134, 162–165, 382/168, 181, 192, 194, 203, 219, 232, 254, 382/274, 276, 291, 298, 305, 213; 702/19; 536/23.1; 435/3
See application file for complete search history.

(56) References Cited

U.S. PATENT DOCUMENTS 5,526,258 A  *  6/1996  Bacus  ........................ 382/129

(Continued)

FOREIGN PATENT DOCUMENTS

| WO | WO 93/21511 |   | 10/1993 |
| WO | WO 02/47/032 | * | 6/2002 |
| WO | WO 02/47032 |   | 6/2002 |

OTHER PUBLICATIONS

Sundbland et al. "The use of Image analysis and automatio for measuring mitotic index in apical conifer meristems", Journal of Experimental Botany, pp. 1749-1756 (1998).*

(Continued)

*Primary Examiner*—Seyed Azarian
(74) *Attorney, Agent, or Firm*—McDonnell Boehnen Hulbert & Berghoff LLP

(57) ABSTRACT

A method of measurement of mitotic activity from histopathological specimen images initially identifies image pixels with luminances corresponding to mitotic figures and selects from them a reference pixel to provide a reference color. Pixels similar to the reference color are located; image regions are grown on located pixels by adding pixels satisfying thresholds of differences to background and image region luminances. Grown regions are thresholded in area, compactness, width/height ratio, luminance ratio to background and difference between areas grown with perturbed thresholds. Grown regions are counted as indicating mitotic figures by thresholding region number, area and luminance. An alternative method of measuring mitotic activity measures a profile of an image region and counts the image region as corresponding to a mitotic figure if its profile is above a threshold at an intensity associated with mitotic figures. A mitotic figure is also indicated if the profile does not meet the previous criterion but has three other values satisfying respective threshold criteria.

34 Claims, 4 Drawing Sheets

U.S. PATENT DOCUMENTS

| | | | |
|---|---|---|---|
| 6,261,760 B1 * | 7/2001 | Fielding et al. | 435/4 |
| 6,876,760 B1 * | 4/2005 | Vaisberg et al. | 382/129 |
| 7,016,787 B2 * | 3/2006 | Vaisberg et al. | 702/19 |
| 7,176,293 B1 * | 2/2007 | Halazonetis et al. | 536/23.1 |
| 7,177,454 B2 * | 2/2007 | McLaren et al. | 382/128 |

OTHER PUBLICATIONS

Madachy et al., "Image Analysis for Automatic Classification of Mitotic Cervical Cells", IEEE Proceedings in Medicine & Biology Society, pp. 372-374 (1988).

Mousa, et al., Feature Analysis and Classification of Chromosome 16 Homologs Using Fluorescence Microscopy Images, Proceedings of the 1999 IEEE Canadian Conference on Electrical and Computer Engineering, pp. 841-845 (May 9-12, 1999).

Cosio, et al., "A Neutral Network Based Workstation for Automated Cell Proliferation Analysis", 2001 Proceedings of the 23rd Annual EMBS Int'l Conference, Oct. 25-28, pp. 2567-2569.

Vega-Alvarado et al., Automatic Metaphase Finding by Inter-Chromosome Extrema Profile Analysis, 2001 Proceedings of the 23rd Annual EMBS Int'l Conference, Oct. 25-28, pp. 2560-2562.

Tomura, et al., "Feature Extraction and Classification of Cell Morphology in Response to the Cell Cycle", Systems and Computers in Japan 20(Mar. 1989) No. 3, pp. 22-30.

* cited by examiner

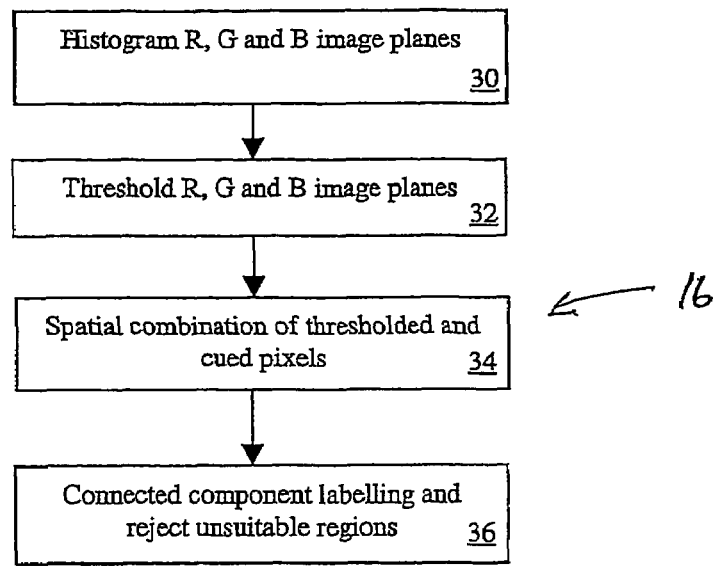
Figure 2 Mitosis feature cueing
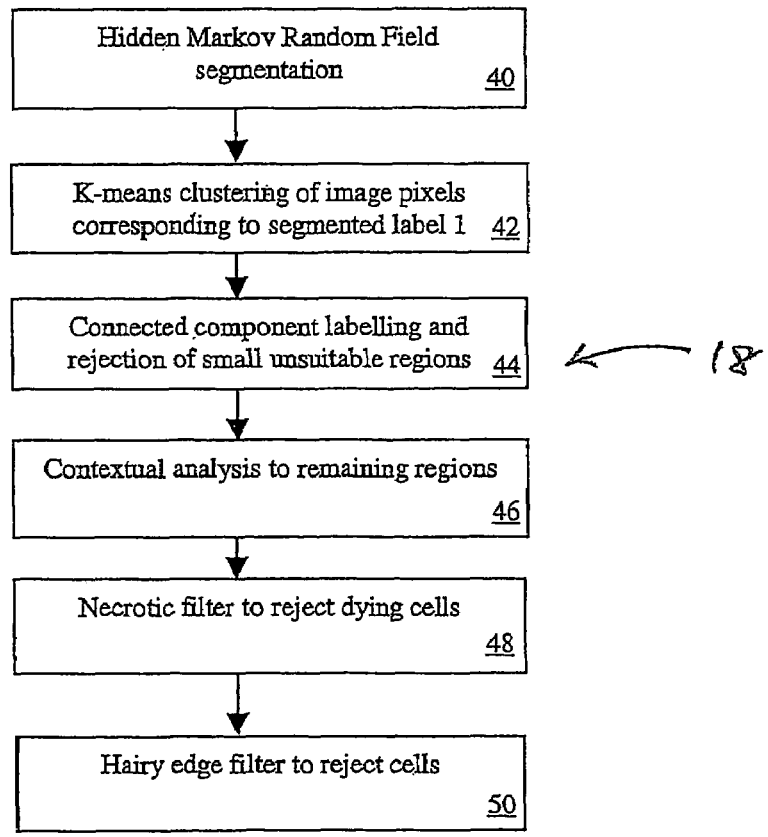
Figure 3 Alternative mitosis feature cueing

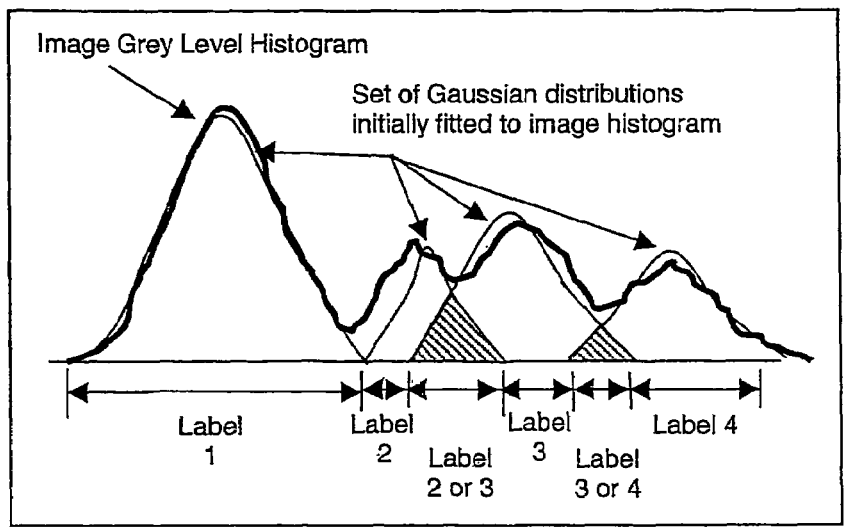
Figure 4; Hidden Markov Random Field Segmentation
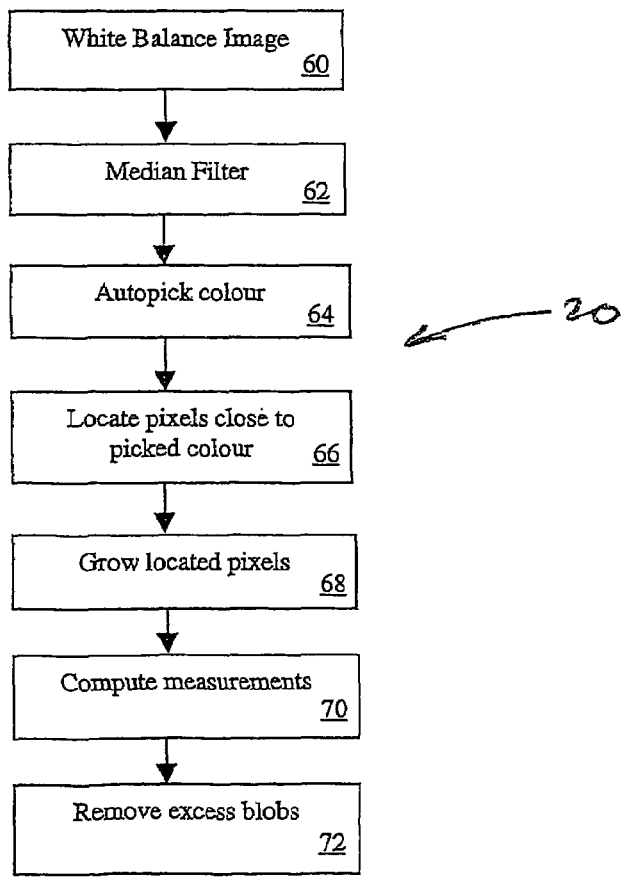
Figure 5 Mitosis Feature Detection

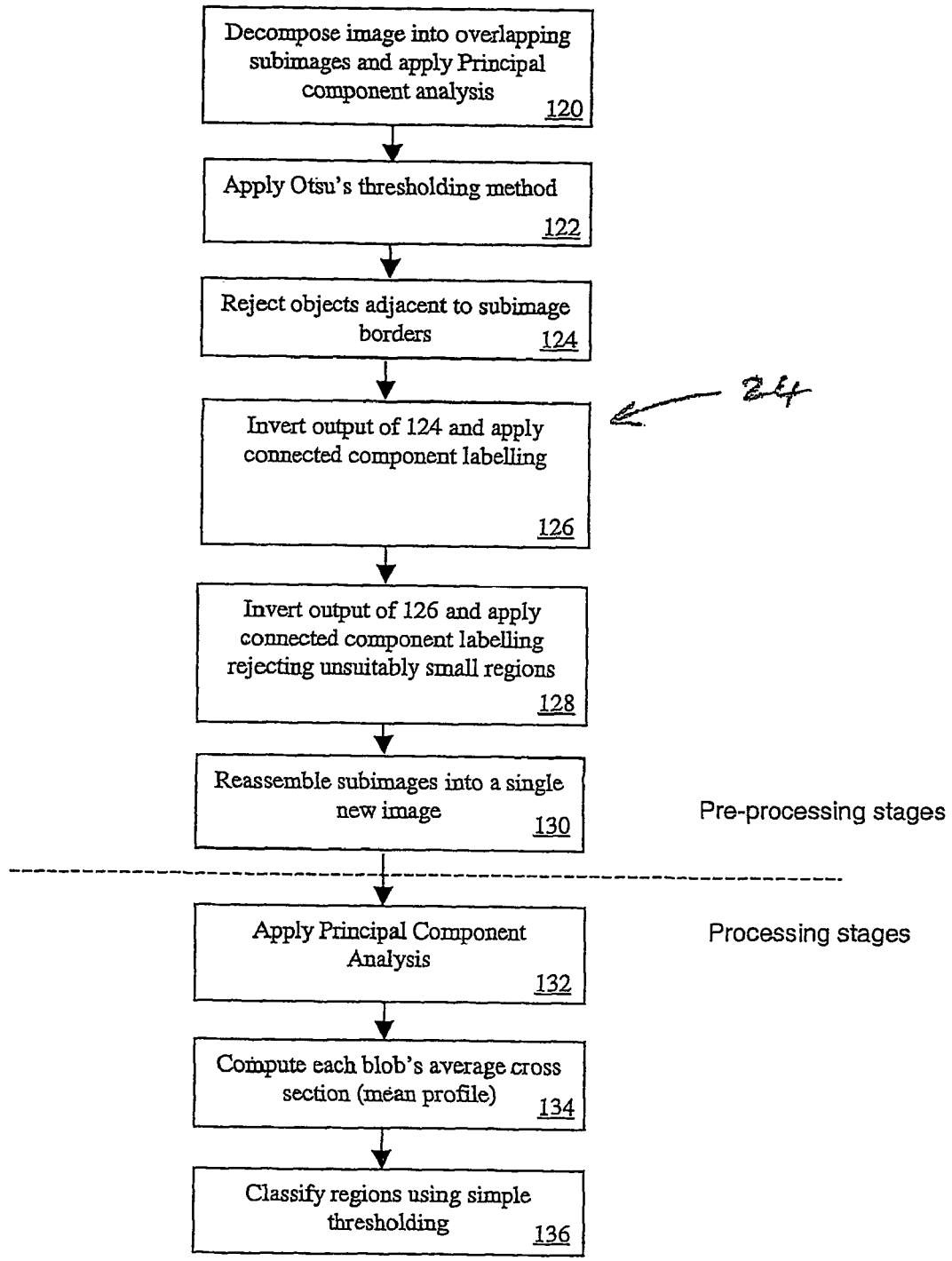
Figure 6 Mitosis feature detection process

MEASUREMENT OF MITOTIC ACTIVITY

This invention relates to a method, an apparatus and a computer program for measurement of mitotic activity, which indicates cell division taking place in a tissue specimen: it is particularly relevant to making measurements on potentially cancerous tissue such as breast cancer tissue. The method is also relevant to other forms of cancer such as colon and cervical cancer.

Breast cancer is a common form of female cancer, and also occurs to a lesser extent in the male: once a lesion indicative of breast cancer has been detected, tissue samples are taken and examined by a histopathologist to establish a diagnosis, prognosis and treatment plan. However, pathological analysis of tissue samples is a time consuming and inaccurate process. It entails interpretation of images by human eye, which is highly subjective: it is characterised in particular by considerable subjectivity in observations of the same samples by different observers and even by the same observer at different times. For example, two different observers assessing the same ten tissue samples may give different opinions for three of the slides—30% error. The problem is exacerbated by heterogeneity, i.e. complexity of some tissue sample features.

Published International Application No. WO 02/47032 A1 relates to measurement of DNA in cells from cell images to indicate mitotic phase. It refers to the use of other image analysis parameters giving one example, magnitude of intensity variance, but does not give details of how this variance can be used to indicate mitotic activity.

There is a need to provide an objective form of measurement of mitotic activity to inform a pathologist's diagnosis and patient treatment.

In one aspect, the present invention provides a method of measuring mitotic activity from histopathological specimen image data, characterised in that the method has the steps of:
a) identifying pixels in the image data having luminances associated with mitotic figures;
b) selecting from among the identified pixels a reference pixel which is sufficiently close in position and luminance to another identified pixel to provide a reference colour;
c) locating pixels in the image data with luminances sufficiently close to that of the reference colour to indicate potentially mitotic figures;
d) incrementing image regions corresponding to potentially mitotic figures from the located pixels by adding pixels thereto, potential increments, to image regions being implemented or rejected by according to whether or not their luminances are sufficiently close to respective image region luminances and sufficiently far from an image data background luminance;
e) selecting grown image regions on the basis of thresholds for image region area, compactness and width/height ratio; and
f) counting selected grown image regions as actually indicating mitotic figures on the basis of a thresholds for number of such regions.

The invention provides the advantage that it provides an objective measurement of mitotic activity to inform a pathologist's diagnosis and patient treatment.

The step of selecting grown image regions may also involve thresholds for ratio of image region luminance to background luminance and area difference between areas derived by growing each image region with multiple thresholds. The thresholds for image region area, compactness, width/height ratio, luminance and area difference may be: 355 pixels<area<1700 pixels, 0.17<compactness<0.77, width/height ratio<2.7, luminance percentage<44%, area difference<23 area/100.

The step of counting selected grown image regions may also involve thresholds for region area and luminance. Successive potential increments to image regions may be individual pixels each of which is an immediate row or column neighbour of an existing image region pixel. Step b) may implemented with, a reference pixel having a luminance differing by less than 8% compared to another identified pixel distant from it by not more than two percent of a smaller of two image dimensions.

Step a) may include white balancing and median filtering the image data prior to identifying pixels having luminances corresponding to mitotic figures. In step c) pixels may be cued for acceptance or rejection as regards indicating mitotic figures by:
a) thresholding colour image data to remove pixels lacking intensities associated with mitotic figure imagery,
b) removal pixels not present in all colours, and
c) thresholding image region areas to remove those too small and too large to be potential mitotic figures.

In step c) pixels may alternatively be cued for acceptance or rejection as regards indicating mitotic figures by:
a) segmenting to identify pixels with intensities associated with mitotic figure imagery,
b) thresholding image region areas to remove those too small and too large to be potential mitotic figures,
c) cluster analysis to determine whether or not a pixel's image region is in a sufficiently large cluster, and
d) necrotic and hairy edge filtering.

In another aspect, the present invention provides a method of measuring mitotic activity from histopathological specimen image data, characterised in that the method has the steps of:
a) measuring an intensity profile of an image region corresponding to a potentially mitotic figure,
b) counting the image region as indicating a mitotic figure if its profile has a value greater than a prearranged threshold at a position in the profile having intensity associated with mitotic figure imagery.

This aspect preferably includes counting the image region as indicating a mitotic figure if its profile has a first value not greater than the prearranged threshold at a position in the profile having intensity associated with mitotic figure imagery, a second value greater than a prearranged second threshold, a third value greater than a prearranged third threshold, and a minimum value less than a prearranged fourth threshold. The first value may be at one end of the profile, the first and second values may adjoin one another in the profile and the third value may not adjoin the second value.

The image data may comprise a first Principal Component obtained by Principal Component Analysis (PCA) of coloured image data, and step a) may include preprocessing image data by:
a) decomposing the image data into overlapping sub-images,
b) applying PCA to the sub-images to derive a first Principal Component image,
c) thresholding the first Principal Component image to produce a binary image of blobs and background
d) rejecting blobs adjacent to or intersecting sub-image boundaries,
e) filling holes in blobs,
f) rejecting blobs too small to correspond to potential mitotic figures, and
g) reassembling the sub-images into a single image for image region profile measurement as aforesaid in step a).

After step g) pixels may be cued for acceptance or rejection as regards indicating mitotic figures by:
a) thresholding colour image data to remove pixels lacking intensities associated with mitotic figure imagery,
b) removal pixels not present in all colours, and
c) thresholding image region areas to remove those too small and too, large to be potential mitotic figures.

After step g) pixels may alternatively be cued for acceptance or rejection as regards indicating mitotic figures by:
a) segmenting to identify pixels with intensities associated with mitotic figure imagery,
b) thresholding image region areas to remove those too small and too large to be potential mitotic figures,
c) cluster analysis to determine whether or not a pixel's image region is in a sufficiently large cluster, and
d) necrotic and hairy edge filtering.

In another aspect, the present invention provides computer apparatus for measuring mitotic activity from histopathological specimen image data, characterised in that it is programmed to execute the steps of:
a) identifying pixels in the image data having luminances associated with mitotic figures;
b) selecting from among the identified pixels a reference pixel which is sufficiently close in position and luminance to another identified pixel to provide a reference colour;
c) locating pixels in the image data with luminances sufficiently close to that of the reference colour to indicate potentially mitotic figures;
d) incrementing image regions corresponding to potentially mitotic figures from the located pixels by adding pixels thereto, potential increments to image regions being implemented or rejected by according to whether or not their luminances are sufficiently close to respective image region luminances and sufficiently far from an image data background luminance;
e) selecting grown image regions on the basis of thresholds for image region area, compactness and width/height ratio; and
f) counting selected grown image regions as actually indicating mitotic figures on the basis of a thresholds for number of such regions.

Computer apparatus for measuring mitotic activity from histopathological specimen image data, characterised in that it is programmed to execute the steps of:
a) measuring an intensity profile of an image region corresponding to a potentially mitotic figure,
b) counting the image region as indicating a mitotic figure if its profile has a value greater than a prearranged threshold at a position in the profile having intensity associated with mitotic figure imagery.

In yet another aspect, the present invention provides a computer program for use in measuring mitotic activity from histopathological specimen image data, characterised in that the computer program contains instructions to control a computer to implement the steps of:
a) identifying pixels in the image data having luminances associated with mitotic figures;
b) selecting from among the identified pixels a reference pixel which is sufficiently close In position and luminance to another identified pixel to provide a reference colour;
c) locating pixels in the image data with luminances sufficiently close to that of the reference colour to indicate potentially mitotic figures;
d) incrementing image regions corresponding to potentially mitotic figures from the located pixels by adding pixels thereto, potential increments to image regions being implemented or rejected by according to whether or not their luminances are sufficiently close to respective image region luminances and sufficiently far from an image data background luminance;
e) selecting grown image regions on the basis of thresholds for image region area, compactness and width/height ratio; and
f) counting selected grown image regions as actually indicating mitotic figures on the basis of a thresholds for number of such regions.

In an additional aspect, the present invention provides a computer program for use in measuring mitotic activity from histopathological specimen image data, characterised in that its instructions provide for implementing the steps of:
a) measuring an intensity profile of an image region corresponding to a potentially mitotic figure, and
b) counting the image region as indicating a mitotic figure if its profile has a value greater than a prearranged threshold at a position in the profile having intensity associated with mitotic figure imagery.

The computer apparatus and computer program aspects of the invention may have preferred features equivalent to corresponding method aspects of the invention.

In order that the invention might be more fully understood, embodiments thereof will now be described, by way of example only, with reference to the accompanying drawings, in which:

FIG. 2 shows in more detail mitosis cueing in the procedure of FIG. 1;

FIG. 3 is a block diagram of an alternative approach to mitosis cueing in the procedure of FIG. 1;

FIG. 4 illustrates the use of hidden Markov random field segmentation in the FIG. 3 mitosis cueing procedure;

FIG. 5 shows in more detail mitosis feature detection in the procedure of FIG. 1; and FIG. 6 is a block diagram of an alternative approach to mitosis feature detection in the procedure of FIG. 1.

Figure 1:
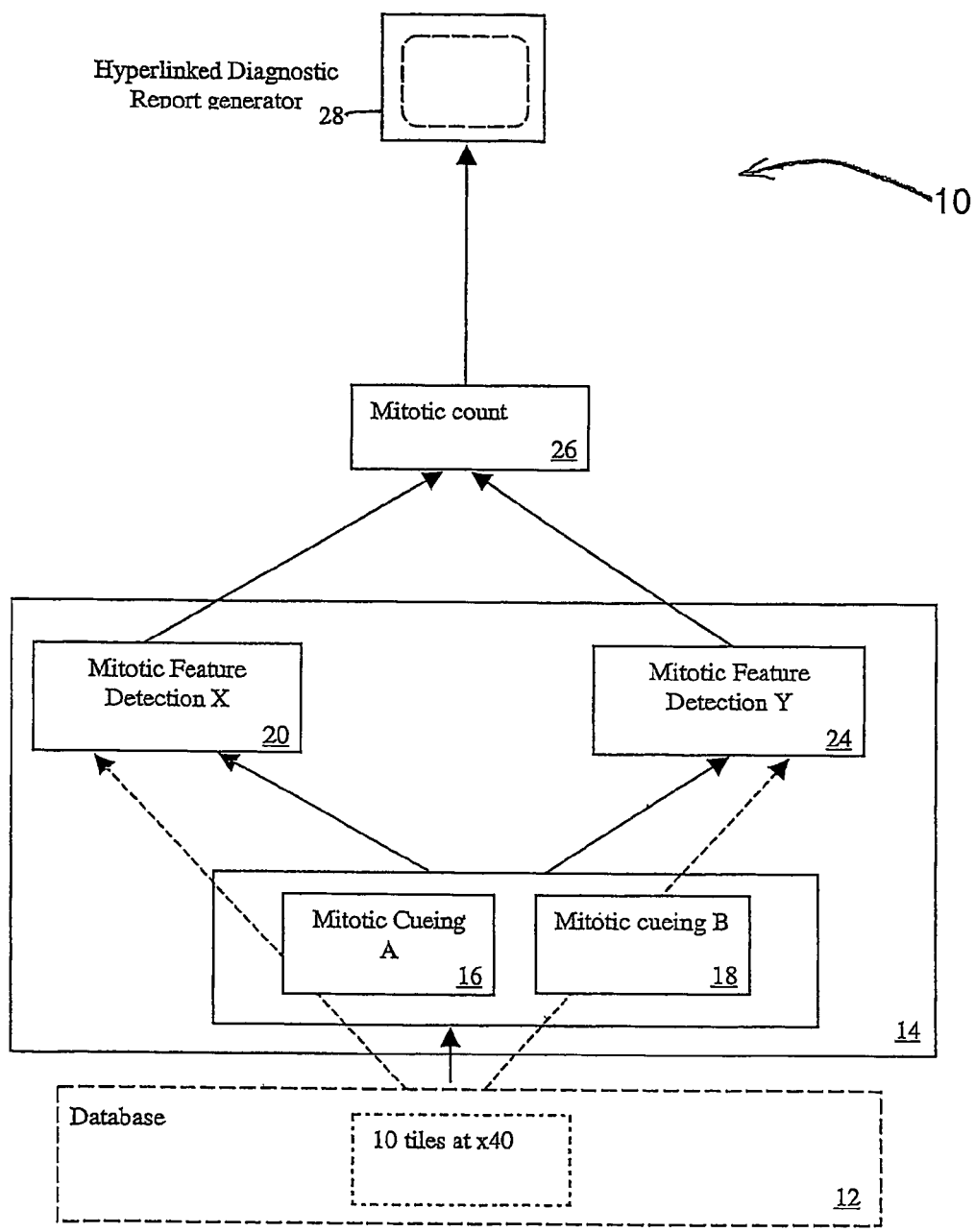
FIG. 1 is a block diagram of a procedure for measuring mitosis activity of the invention, and incorporating mitosis cueing, feature detection and counting.

Referring to FIG. 1, a procedure 10 for the assessment of tissue samples in the form of histopathological slides of potential carcinomas of the breast is shown. This drawing illustrates processes for measuring mitotic activity to produce a parameter for use by a pathologist as the basis for assessing patient diagnosis.

The procedure 10 employs a database 12, which maintains digitised image data obtained from histological slides as will be described later. Sections are taken (cut) from breast tissue samples (biopsies) and placed on respective slides. Slides are stained using the staining agent haematoxylin & eosin (H&E), which is a common stain for delineating tissue and cellular structure. Tissue stained with H&E is used to assess mitotic activity.

Measurement of mitotic activity in a tissue specimen gives an indication of the degree of cell division that is taking place. A histopathological slide is a snap shot representing a very short time interval in a cell division process, so the chance of such a slide showing a particular phase of mitotic activity is very small: if such a phase is in fact present in a slide, that is a good indicator of how fast a potential tumour is growing.

In a prior art manual procedure for scoring mitotic activity, a clinician places a slide under a microscope and examines a region of it (referred to as a tile) at magnification of ×40 for indications of mitotic activity. This manual procedure involves a pathologist subjectively and separately estimating unusual colour, size, shape and boundary definition of cells in a tissue sample. The values obtained in this way are combined by the pathologist to give a single measurement for use in diagnosis. The process hereinafter described in this example replaces the prior art manual procedure with an objective procedure.

The invention uses image data from histological slides. In the present example, image data were obtained by a pathologist using Zeiss Axioskop microscope with a Jenoptiks Progres 3012 digital camera. Image data from each slide is a set of digital images obtained at a linear magnification of 40 (i.e. 40×), each image being an electronic equivalent of a tile.

To select images, a pathologist scans the microscope over a slide, and at 40× magnification selects regions (tiles) of the slide which appear to be most promising in terms of analysing of mitotic activity. Each of these regions is then photographed using the microscope and digital camera referred to above, and this produces for each region a respective digitised image in three colours, i.e. red, green and blue (R, G & B). Three intensity values are obtained for each pixel in a pixel array to provide an image as a combination of R, G and B image planes. This image data is stored temporarily at 12 for later use. Ten digitised images are required for measurement of mitotic activity at 14 which then provides input to a diagnostic report at 28.

A number of alternative processes 16 to 24 will be described to measure mitotic activity in a given sample: these comprise two alternative mitotic cueing processes 16 and 18 and two alternative mitotic feature detection processes 20 and 24. The measure of mitotic activity is converted at 26 into a mitotic count for use by a pathologist.

Referring now to FIG. 2, the first alternative mitotic cueing process 16 is shown in more detail. If it is selected for, use, it is carried out for each of the ten digitised images mentioned above, but will now be described for one such image referred to as the input image. It is used to cue or identify dark image regions, which may correspond to mitotic cells.

At a stage 30, from the input image three histograms are formed showing the occurrence frequency of pixel intensities, one histogram representing R (red) intensities, one B (blue) and one G (green). For example, an image with 8 bits per colour per pixel would have a histogram abscissa axis of 256 intensity values, 0 to 255, and a histogram ordinate axis of number of pixels in the image having each intensity value. Each histogram is a vector having 256 elements, and the ith element (i=0 to 255) of each vector is the number of pixels having intensity i in the R, G or B image plane.

The next stage is to threshold the R, G or B image planes at 32: to implement this, firstly the total number $N_T$ of pixels in an image plane is counted (this will be the same value for all three image planes). For each image plane $N_T$ is then divided by a respective empirical R, G or B parameter $P_R$, $P_G$ or $P_B$ determined from experience of implementing the invention: parameter values $P_R=100$, $P_G=100$ and $P_B=140$ were derived manually and empirically from a set of 250 test images obtained using the Zeiss Axioskop microscope and Jenoptiks Progres 3012 camera mentioned above. Images produced using a different microscope/camera combination might require different parameters. This procedure gives three thresholds $T_R$, $T_G$ and $T_B$ equal respectively to $N_T/P_R$, $N_T/P_G$ and $N_T/P_B$.

The histograms and the thresholds $T_R$, $T_G$ and $T_B$ are then used for each image plane to select low intensity pixels whose total number does not exceed the threshold $T_R$, $T_G$ or $T_B$. So for example an image having a total number of pixels $N_T$ equal to 20,000 would have a red and green image planes with $P_R=100$, $P_G=100$ and $T_R$ and $T_G$ equal to 200. For the blue image plane $T_B$ is $2 \times 10^4/140$ or ~142. In an eight-bit range of pixel intensities with values 0 to 255, the red image plane histogram might have numbers of pixels 3, 20, 50, 7, 20, 80 and 65 at pixel intensity values 0 to 6 respectively. The total number of pixels having pixel intensity values 0 to 6 is 245, which exceeds the red image plane threshold $T_R$ of 200; however the total number over pixel intensity values 0 to 5 is less than 200, and these are therefore retained and pixels with intensity values 6 to 255 are rejected. The procedure retains a small part of the histogram, which corresponds to the darker regions of the red image plane (mitotic cells tend to be dark). This procedure is repeated for the green and blue image planes using their respective thresholds. The objective is to retain in each image plane a number of pixels which are likely to be in proportion to the number of pixels in the image.

The next stage 34 is spatial filtering: here the red, green and blue retained pixels are compared and every pixel which is not retained in all three image planes after thresholding is rejected. Each pixel remaining after spatial filtering is then cued by assigning it a binary 1 value and all other pixels in the image which have rejected are set to binary 0: this creates a single combined binary image for output from the stage 34.

At 36, a technique known as "connected component labelling" (CCL) is applied to the combined binary image from stage 34: this is a known image processing technique (sometimes referred to as 'blob colouring') published by Klette R., Zamperoniu P., 'Handbook of Image Processing Operators', John Wiley & Sons, 1996, and Rosenfeld A., Kak A. C., 'Digital Picture Processing', vols. 1 & 2, Academic Press, New York, 1982. CCL gives numerical labels to image regions which are "blobs" in the binary image, blobs being groups of contiguous or connected pixels of the same value 1 in a binary image containing 0s and 1s only: each group or blob is assigned a number (label) different to those of other groups to enable individual blobs to be distinguished from others. CCL also provides blob areas in terms of number of pixels.

Blobs are then retained (pixels set to 1) or rejected (pixels set to 0) based on their dimensions: blobs are retained if they both contain from 95 to 5000 pixels inclusive and have height and width of not more than 2000 pixels. In this example the minimum area of 95 pixels is deliberately set to a small value to avoid rejecting too many blobs that might be of interest for possible mitotic activity. The maximum area is set to a large value for the same reason. The output of stage 36 is a binary image containing a set of labelled blobs for analysis for mitotic activity as will be described later. Stage 36 is useful for removing blobs which aren't likely to be relevant for later processing, but it is not essential.

Referring now to FIG. 3, the second mitotic cueing process 18 is shown in more detail. As in the previous example, if the process 18 is selected for use, it is carried out for each of the ten digitised images mentioned above, but will now be described for one such image. At a stage 40 a single iteration of a technique known as "Hidden Markov Random Field segmentation" is performed on the red component of an original (RGB) input image of a tile. This segmentation is a known image processing technique, see by Devijver P. A., 'Image segmentation using causal Markov Random Field models', Pattern Recognition, J.Kittler (ed) Lecture Notes in Computer Science 301, Springer-Verlag 1988; also Ducksbury P. G., 'Parallel model based segmentation using a $3^{rd}$ order hidden Markov model', $4^{th}$ IEE Int. Conf. Image Processing and its Applications, Maastricht, 7-9 Apr. 1992. The input image is quantised into four levels (i.e. reduced from potentially 256 grey levels to just four): the first of these levels corresponds to very dark areas of the input image, second and third levels are progressively less dark and the fourth level corresponds to light image areas. The input image's grey level histogram is computed and initially fitted with a set of four Gaussian distributions of number of pixels N(x) as a function of pixel value x, the distributions having a variety of means μ and standard deviations σ and each being of the form:

$$N(x) = \frac{1}{\sqrt{(2\pi)}\sigma} e^{-(x-\mu)^2/2\sigma^2} \quad (1)$$

In this example, the Equation (1) distributions form the basis of image segmentation, which is defined as separation of objects from a background in a digital image. The Gaussian distributions are numbered 1 to 4 respectively. If an image pixel has a grey level that falls within Gaussian distribution number j (j=1, 2, 3 or 4), then its segmented label is j. However where there is overlap of Gaussians as in shaded areas in FIG. 4 then the power of the Markov segmentation algorithm comes into effect in making a probabilistic decision as to which is the best segmented label to choose. The output from this stage 40 is a mask image where each pixel has been allocated one of four numbers (1, 2, 3 or 4). Only pixels having label 1 (corresponding to dark image areas) are used in subsequent processing stages. Even though only label 1 pixels are retained, for good image segmentation it is better to use an adequate number of levels or labels (four in this case) and to assign pixels correctly: this improves the results for label 1. Using too few segmentation levels, segmented regions may be too large and contain inappropriate pixels; with too many levels, segmented regions may be too small and fragmented.

Segmentation into four is found to be a good compromise, despite using only lowest numbered pixels in later processing. Stage 40 is a useful segmentation technique but others can be used instead.

At 42 a K-means clustering process is performed: this is a known process which is described by J. A. Hartigan and M. A. Wong in a paper entitled 'A K-means clustering algorithm', Algorithm AS 136, Applied Statistics Journal, 1979. K-means is an iterative statistical technique for computing an optimal set of clusters (groups of data items sharing some common property) from a dataset. This process uses raw image pixels from the red component of the original (RGB) input image of a tile input at 40: it selects those red pixels that are located in the same image position as pixels labelled 1 in the mask image generated at 40. Designating the maximum and minimum of the values of the label 1 raw image pixels as "max" and "min" respectively, three clusters are used and initially cluster centres for the K-means technique are set relative to the dynamic range (max-min) of these pixels as follows:

| Cluster | Initial cluster centre setting | |
| --- | --- | --- |
| 1 | min + 0.1 × (max − min) | 10% of dynamic range above min |
| 2 | min + 0.5 × (max − min) | middle of dynamic range |
| 3 | max − 0.1 × (max − min) | 10% of dynamic range below max |

From the result of the K-means technique-two masks are created: one mask marks areas containing cluster 1 OR cluster 2 (the joint cluster mask) whilst the second mask marks just cluster 1 in isolation (the cluster 1 mask). Only clusters 1 and 2 are required for later processing; the third cluster is used simply to separate data on a more reasonable basis.

At 44 connected component labelling (CCL, as previously described) is applied to the mask created at 42 which marks the joint cluster (cluster 1 OR cluster 2). CCL also gives the areas of labelled blobs in terms of numbers of pixels. Blobs that are outside an allowed area range are rejected, and those within this range are retained as indicated in the table below and renumbered sequentially from label 1 upwards. The output from stage 44 is a set of labelled blobs.

| | |
| --- | --- |
| EITHER blob size < 70 pixels OR size > 262144 pixels | Reject blob - set all its pixels to 0 and exclude from set of labelled blobs |
| 70 pixels ≦ blob size ≦ 262144 pixels | Accept for further processing and include in set of labelled blobs |

The maximum and minimum acceptable blob areas (262144 and 70 pixels) were chosen to be sufficiently widely separated to avoid significant loss of potentially relevant blobs—this dynamic range might be reducible if more knowledge of relevant blob sizes becomes available. Stage 44 is useful to remove unwanted blobs but could be dispensed with.

At 46 each labelled blob generated at 44 is considered and accepted or rejected based on a contextual analysis of its cluster 1/(cluster 1+cluster 2) score; i.e. from the results of 42, for each blob find how Many of its pixels are in cluster 1 (NC1) and how many in cluster 2 (NC2): then calculate the ratio NC1/(NC1+NC2), and accept the blob for further processing if this ratio is 0.6 or greater. Reject the blob if the ratio is less than 0.6. The result is a reduced set of blobs.

| | |
| --- | --- |
| Contextual measure ≧ cluster context threshold (60%) | Accept for further processing into set of blobs |
| Contextual measure < cluster context threshold (60%) | Reject blob |

At 48 take the reduced set of blobs generated at 46 and perform a rejection using a 'necrotic filter': such a filter computes a standard metric referred to as the Euclidean metric $M_{Eu}$ of normalised quantised boundary phase (as described later). The Euclidean metric $M_{Eu}$ is of the form:

$$M_{Eu} = \sqrt{\sum_{i=1}^{n} (x_i - y_i)^2} \quad (2)$$

where $x_i$ and $y_i$ (i=1 to n) are elements of vectors x and y respectively representing the two quantities to be compared. The 'necrotic filter' process is as follows: firstly, a Sobel edge filter is applied to the labelled image obtained from step 44 and the raw image—i.e. the red component of the original (RGB) input image input to stage 40 tile. The labelled image is used to obtain the boundary of the blob that may correspond to a mitotic figure and the raw image is used to obtain the phase angle of pixels in the raw image. Sobel is a standard image processing technique published in Klette R., & Zamperoni P., 'Handbook of image processing operators', John Wiley & Sons, 1995. A Sobel filter consists of two 3×3 arrays of numbers $S_P$ and $S_Q$, each of which is convolved with successive 3×3 arrays of pixels in an image. Here $$S_P = \begin{bmatrix} 1 & 2 & 1 \\ 0 & 0 & 0 \\ -1 & -2 & -1 \end{bmatrix} \text{ and } S_Q = \begin{bmatrix} 1 & 0 & -1 \\ 2 & 0 & -2 \\ 1 & 0 & -1 \end{bmatrix} \quad (3)$$

A first 3×3 array of pixels is selected in the top left hand corner of the labeled image: designating as $C_{ij}$ a general labelled pixel in row i and column j, the top left hand corner of the image consists of pixels $C_{11}$ to $C_{13}$, $C_{21}$ to $C_{23}$ and $C_{31}$ to $C_{33}$. $C_{ij}$ is then multiplied by the respective digit of $S_P$ located in the $S_P$ array as $C_{ij}$ is in the 3×3 cyan pixel array: i.e. $C_{11}$ to $C_{13}$ are multiplied by 1, 2 and 1 respectively, $C_{21}$ to $C_{23}$ by zeroes and $C_{31}$ to $C_{33}$ by —1, −2 and −1 respectively. The products so formed are added algebraically and provide a value p. The value of p will be relatively low for pixel values changing slowly between the first and third rows either side of the row of $C_{22}$, and relatively high for pixel values changing rapidly between those rows: in consequence p provides an indication of edge sharpness across rows. This procedure is repeated using the same pixel array but with $S_Q$ replacing $S_P$, and a value q is obtained: q is relatively low for pixel values changing slowly between the first and third columns either side of the column of $C_{22}$, and relatively high for pixel values changing rapidly between those columns, and q therefore provides an indication of edge sharpness across columns. The square root of the sum of the squares of p and q are then computed i.e. $\sqrt{p^2+q^2}$, which is defined as an "edge magnitude" and becomes $T_{22}$ (replacing pixel $C_{22}$ at the centre of the 3×3 array) in the transformed image. $\tan^{-1}p/q$ is also obtained at each pixel and is defined as a "phase angle".

A general pixel $T_{ij}$ (row i, column j) in the transformed image is derived from $C_{i-1,j-1}$ to $C_{i-1,j+1}$, $C_{i,j-1}$ to $C_{i,j+1}$ and $C_{i+1,j-1}$ to $C_{i+1,j+1}$ of the labeled image. Because the central row and column of the Sobel filters in Equation (3) respectively are zeros, and other coefficients are 1s and 2s, p and q for $T_{ij}$ can be calculated as follows:

$$p = \{C_{i-1,j-1} + 2C_{i-1,j} + C_{i-1,j+1}\} - \{C_{i+1,j-1} + 2C_{i+1,j} + C_{i+1,j+1}\} \quad (4)$$

$$q = \{C_{i-1,j-1} + 2C_{i,j-1} + C_{i+1,j-1}\} - \{C_{i-1,j+1} + 2C_{i,j+1} + C_{i+1,j+1}\} \quad (5)$$

Beginning with i=j=2, p and q are calculated for successive 3×3 pixel arrays by incrementing j by 1 and evaluating Equations (2) and (3) for each such array until the end of a row is reached; j is then incremented by 1 and the procedure is repeated for a second row and so on until the whole image has been transformed. The Sobel filter cannot calculate values for pixels at image edges having no adjacent pixels on one or other of its sides: i.e. in a pixel array having N rows and M columns, edge pixels are the top and bottom rows and the first and last columns, or in the transformed image pixels $T_{11}$ to $T_{1M}$, $T_{N1}$ to $T_{NM}$, $T_{11}$ to $T_{1M}$ and $T_{1M}$ to $T_{NM}$. By convention in Sobel filtering these edge pixels are set to zero. The output of the Sobel filter comprises two transformed images, one (the edge filtered image) contains the boundaries of the labeled blobs produced at 44 whilst the other contains the "phase angle" of the raw input image.

A pixel of a labelled blob is a boundary pixel if the like-located pixel in the Sobel edge filtered image is non-zero: for each boundary pixel the phase angle is extracted from the like-located pixel in the Sobel phase angle image. This phase angle information is then quantised to reduce it to four orientation ranges (0-44, 45-89, 90-134, 135-179 degrees) and the number of boundary pixels in each orientation is normalised by dividing it by the number of pixels in the perimeter of the blob. This results in a respective 4-element vector of normalised orientations or quantised phase for each blob: The Euclidean measure of each of these vectors is computed using Equation (2) and compared with that of a perfect circle, in which the four vector elements are of equal value. This searches for blobs relatively far from circularity. The Euclidean measures of the labelled blobs are compared with a Euclidean Threshold of 0.4354 and are rejected if they are greater than it. The Euclidean threshold was derived from a K-means analysis of a test dataset. Output a set of remaining blobs.

| | |
|---|---|
| Euclidean measure > 0.4354 | Reject blob |
| Euclidean measure ≦ 0.4354 | Accept blob for further processing as part of a set of remaining blobs |

At 50 each of the blobs remaining after step 48 is examined and a 'hairy edge filter' operation is performed. A 'hairy edge filter' measures the amount of edge structure in an area around a blob, this being a rough approximation to the 'hairy fibres' sometimes seen around mitotic figures. This is computed for each blob as follows:

a) Two morphological dilations are applied using filters 5×5 and 13×13 pixels in size as shown below.

$$5\times5 \text{ filter} = \begin{matrix} 0 & 0 & 1 & 0 & 0 \\ 0 & 1 & 1 & 1 & 0 \\ 1 & 1 & 1 & 1 & 1 \\ 1 & 1 & 1 & 1 & 0 \\ 0 & 0 & 1 & 0 & 0 \end{matrix} \quad (6)$$

$$13\times13 \text{ filter} = \begin{matrix} 0 & 0 & 0 & 0 & 0 & 0 & 1 & 0 & 0 & 0 & 0 & 0 & 0 \\ 0 & 0 & 0 & 1 & 1 & 1 & 1 & 1 & 1 & 1 & 0 & 0 & 0 \\ 0 & 0 & 1 & 1 & 1 & 1 & 1 & 1 & 1 & 1 & 1 & 0 & 0 \\ 0 & 1 & 1 & 1 & 1 & 1 & 1 & 1 & 1 & 1 & 1 & 1 & 0 \\ 0 & 1 & 1 & 1 & 1 & 1 & 1 & 1 & 1 & 1 & 1 & 1 & 0 \\ 0 & 1 & 1 & 1 & 1 & 1 & 1 & 1 & 1 & 1 & 1 & 1 & 0 \\ 1 & 1 & 1 & 1 & 1 & 1 & 1 & 1 & 1 & 1 & 1 & 1 & 1 \\ 0 & 1 & 1 & 1 & 1 & 1 & 1 & 1 & 1 & 1 & 1 & 1 & 0 \\ 0 & 1 & 1 & 1 & 1 & 1 & 1 & 1 & 1 & 1 & 1 & 1 & 0 \\ 0 & 1 & 1 & 1 & 1 & 1 & 1 & 1 & 1 & 1 & 1 & 1 & 0 \\ 0 & 0 & 1 & 1 & 1 & 1 & 1 & 1 & 1 & 1 & 1 & 0 & 0 \\ 0 & 0 & 0 & 1 & 1 & 1 & 1 & 1 & 1 & 1 & 0 & 0 & 0 \\ 0 & 0 & 0 & 0 & 0 & 0 & 1 & 0 & 0 & 0 & 0 & 0 & 0 \end{matrix} \quad (7)$$

Morphological dilation is an expansion operation: for an original binary image (i.e. having pixel values 1 and 0 only), the expansion operation comprises locating each pixel with value 1 and setting pixels in its vicinity also to 1. In the two above arrays, a central 1 indicates a pixel found to be 1 in the image, other 1s indicate the relative positions of nearby pixels set to 1 to implement morphological dilation, and 0s represent pixels left unchanged.

Morphology is an image processing technique based on shape and geometry. It is a standard image processing procedure published in Umbaugh S. C., 'Colour vision and image processing', Prentice Hall, 1998. Morphology applies a filter of some size and shape to an image. In the simplest sense dilation (dilates (or expands) an object) at each pixel position the output of the dilation is the logical OR of the inputs. The filters used contain approximations to circles as shown above.

The application of the two dilation operations results in two dilated results. Each blob is dilated by two different amounts, as described with reference to Equations (6) and (7): the blob resulting from the 5×5 filter is then subtracted from that resulting from the 13×13 filter, which results in a border around the blob. This is repeated for each of the blobs remaining after step 48.

b) A Sobel filter (as previously described) is applied to obtain the gradient of the raw image—i.e. the red component of the original (RGB) input image of a tile input at 40. A summation of gradient values is formed within the area of the border (mask) determined at a) around each blob and is used as a filter measure for comparison with a Hairy Threshold for acceptance and rejection of blobs as shown in the table immediately below.

| | |
|---|---|
| Filter measure ≧ Hairy Threshold (25000) | Accept blob as valid for processing for mitotic feature detection |
| Filter measure < Hairy Threshold (25000) | Reject blob |

The output of step b) is a set of cued blobs considered valid for use in mitosis feature detection as will be described later. Stages 46, 48 and 50 are desirable to reduce unwanted blobs, but are not essential if the consequent processing burden in mitotic feature detection can be tolerated.

Referring now to FIG. 5, there is shown a flow diagram of the mitotic feature detection process 20, which is carried out for each of the ten digitised input images referred to above and will be described for one image. At a first stage 60, an input RGB image is preferably white balanced by remapping its most luminous pixel to white. For each pixel i (i=1 to total number of pixels in image) in this image, pixel luminance $L_i$ is computed from its red, green and blue Intensities $R_i$, $G_i$ and $B_i$ using the following equation:

$$L_i = 0.299 \times R_i + 0.587 \times G_i + 0.114 \times B_i \quad (8)$$

Then the pixel with the maximum of the luminance values of all pixels in the input (RGB) image is located and used to record the corresponding values of R, G and B at that maximum luminance pixel position and denoted LumMaxR, LumMaxG and LumMaxB. The ratios for each of the three image planes are then computed as $$RatioR = (255/LumMaxR) \times 1.05 \quad (9)$$

$$RatioG = (255/LumMaxG) \times 1.05 \quad (10)$$

$$RatioB = (255/LumMaxB) \times 1.05 \quad (11)$$

The original RGB pixel values are now multiplied by these ratios to produce a white balanced image with three image planes with the following values for each pixel i:

$$BalancedR_i = R_i \times RatioR \quad (12)$$

$$BalancedG_i = G_i \times RatioG \quad (13)$$

$$BalancedB_i = B_i \times RatioB \quad (14)$$

The final stage is to clip the new white balanced image so that no pixel values lie outside the eight bit range (0 to 255). If any pixel value is less than 0, it is set to zero and if any pixel value is greater than 255, it is set to, 255. Production of a white balanced image is not essential but desirable to reduce variation between images.

At 62 the clipped white balanced image from step 60 is filtered with a 3×3 median filter to remove spatial noise (desirable but not essential). The filter is applied independently to each of the balanced red (BalancedR), green (BalancedG) and blue (BalancedB) image planes computed at 60: the median filter operation selects each pixel in these image planes in succession (other than edge pixels) and takes a 3×3 array of those pixels centred on the selected pixel. The 3×3 array of pixels is then sorted into ascending order of pixel value using what is referred to as "quicksort". Quicksort is a known technique published by Klette R., Zamperoniu P., 'Handbook of Image Processing Operators', John Wiley & Sons, 1996, and will not be described. It is not essential but convenient. The median pixel value (fifth of nine) is then taken as the filter output to replace the value of the selected pixel. This is repeated across the clipped white balanced image. Pixels in edge rows and columns do not have the requisite 3×3 array, and for these the clipped white balanced image pixel values are retained in the median filtered image.

At 64 an 'autopick colour' process is applied which picks or locates a pixel having the lowest luminance (darkest) in the median filtered image (excluding outlying pixels relatively remote from pixels of similar luminance): this means that the chosen pixel has at least one relatively nearby pixel with luminance similar to its own. Dark pixels are selected because mitotic figures tend to have relatively low luminance using conventional histological slide preparation techniques. The computation is as follows, for each pixel position in the median filtered image the luminance $L_i$ is computed as follows:

$$L_i = 0.299 \times R_i + 0.587 \times G_i + 0.114 \times B_i \quad (15)$$

Computing $L_i$ for each pixel position in the median filtered image using Equation (15) provides a luminance image: in the luminance image a first pixel value and its location is stored as a current darkest pixel. Successive pixels in that image are compared with the first pixel: if any comparison pixel has $L_i$ darker (lower value of luminance) than the current darkest then its pixel value and its location are stored in a list of darkest pixels. After the list has reached ten entries, the current least dark pixel in it is removed and replaced by a later pixel on each occasion a later pixel is darker than the least dark pixel: this process continues until all pixels have been compared with and where appropriate added to the list. After processing the entire luminance image, the list of darkest pixels is sorted into descending order of darkness using Quicksort (as mentioned above) so that the darkest is first. If the procedure results in, less than ten darkest pixels, the stored comparison luminance value originally obtained from the first pixel is increased and the procedure repeated.

The next step is to determine whether or not the darkest pixel satisfies the condition that it is located relatively near another of the ten darkest pixels: i.e. the condition is that these two pixels be separated by a distance of not more than twenty pixels in any direction (along a row, a column diagonally or between a diagonal and a row or column). This condition applies to an image of dimensions 1476 pixels by 1160 pixels, so the maximum separation is 2% of the smaller image dimension. If this condition is satisfied, a darkest pixel has been located having a comparatively near neighbour of similar luminance and therefore not considered to be an outlying pixel: the luminance of this darkest pixel is denoted by $L_{picked\ colour}$. If the condition is not satisfied then the procedure is iterated by discarding the current darkest pixel from the list and taking the remaining darkest pixel; iteration continues until the condition is met. The list size of ten was determined by analysis of the ten images selected as previously described, but it is not critical and a different number can be chosen. The pixel from which $L_{picked\ colour}$ is taken should therefore be selected from a small group (twenty or less) of the darkest pixels.

At 66 a 'colour proximity highlighting' is carried out which locates image pixels in the median filtered image that have luminances differing from $L_{picked\ colour}$ by less than 20 (i.e. less than 8% for an eight-bit intensity range from 0 to 255). This is carried out by creating a mask image as follows: for each pixel in the median filtered image, if a luminance inequality condition (16) below is true then the pixel is accepted and represented by a value 255 in the equivalent position in the mask image.

$$|(0.299 \times R_i + 0.587 \times G_i + 0.114 \times B_i) - (L_{picked\ colour})| < 20 \qquad (16)$$

If the inequality condition (16) is not true, then the current pixel is rejected and represented by 0 in the mask image. Results from whichever of the cueing processes 16 and 18 has been used are introduced in this step 66: i.e. a pixel for which the inequality condition (16) is true is accepted or rejected according to whether there is a 1 or 0 value respectively for a corresponding pixel located in the same position in the mitosis cued image resulting from process 16 or 18. It is not essential to use a process 16 or 18 but it is useful to reduce processing burden.

At 68 accepted pixels are "grown" so that they come to correspond to a whole cell instead of just part of a cell. Luminance proximity is used to check if growing should continue: i.e. if the mask image computed at 66 indicates that there is too large a luminance difference between a selected pixel and a test pixel as compared to a luminance difference threshold denoted by $L_T$ ($L_T$=75 in this example), growth with the selected pixel does not continue.

The process 68 of growing pixels is as follows: firstly, an image store labelled 'grow' is created that indicates whether pixel positions are 'grown' or 'not grown' and each entry or pixel in 'grow' is initially set to 'false' (false=0) indicating that no pixels have yet been 'grown': 'true' (true=1) would indicate 'grown'. Secondly, a background colour for image 'grow' is computed from the median filtered image by averaging all pixels other than those that are white (i.e. having R, G and B all equal to the maximum value of 255): the value of this background colour is recorded. The growing process now proceeds in accordance with the computer program steps below: in these steps a convention is used that an inset of a line to the right indicates an iterative loop including the line and those following it of equal and greater inset, the loop terminating when a line of lesser inset is reached.

For each pixel in the median filtered image:
If the mask image pixel is accepted and a corresponding pixel in the same location in 'grow' is 0 then:
Set the pixel in 'grow' to true (1)
Enter the position of the pixel in 'grow' in a list entitled 'Action List'
As long as the Action List is not empty then:
Remove the most recently added pixel from the Action List but retain its image position in memory and designate it as the 'removed pixel',
Select four pixels in 'grow' that are nearest neighbours of the removed pixel, i.e. pixels immediately adjacent to the removed pixel in the same column or row only, not diagonal neighbours.
Select one of the nearest neighbour pixels not yet compared with the mask image pixel,
If (and only if) the three following criteria are met, i.e. (a) the mask image pixel and the selected nearest neighbour pixel differ in luminance by less than $L_T$, (b) the mask image pixel and the background colour differ in luminance by more than $L_T$, and (c) the mask image pixel and a white pixel differ in luminance by more than $L_T$, then:
Change from false (0) to true (1) the pixel in 'grow' located in the same position as the selected nearest neighbour pixel, and add the position of the selected nearest neighbour pixel to the Action List
If any one or more of the criteria (a), (b) and (c) are not met, leave the relevant pixel in 'grow' unchanged and do not add its position to the Action List
Repeat for next nearest neighbour pixel not yet compared with the mask image pixel,
Repeat for next entry in the Action list
Repeat for all other mask image pixels.

The above computer program steps provide a mechanism for continuing to grow a cell from an original single pixel in the mask image by reassessing further pixels for growth. Nearest neighbour pixels of a 'seed' mask image pixel to be grown are assessed: each of the nearest neighbours which becomes added (changed to 1) in growth is also added to the Action List for its uncompared nearest neighbours to be assessed. Growth therefore proceeds until all pixels adjoining but not part of a grown cell have been assessed and have failed one or more of the three luminance criteria (a), (b) and (c). Growth then terminates for that cell and restarts for another cell based on a new 'seed' mask image pixel.

The result of 68 is a new image 'grow' which now contains a set of blobs (image regions of contiguous pixels of value 1) which are candidates for indicating positions of real cells that are likely to be of interest for mitosis. The blobs are processed at 70 by connected component labelling as previously described: this derives a set of measurements for each blob as follows:
area A (the number of pixels in a blob),
perimeter P (the number of pixels on a blob's boundary),
compactness ($4\pi A/P^2$),
width (maximum number of pixels in a row across a blob),
height (maximum number of pixels in a column down a blob),
ratio width/height,
luminance percentage: using median filtered image pixels located in the same positions as the pixels of the blob, this measure is computed by multiplying by 100 the result of dividing the luminance of the darkest median filtered image pixels by the luminance of the background colour,
perturbed difference (difference between grown blob sizes obtained using thresholds corresponding to $L_T$ perturbed by a prearranged increment and decrement respectively), and
Hue difference (absolute value of difference between an average Hue and a background Hue from the input image).

The perturbed difference is computed as follows:
the threshold $L_T$ is adjusted by adding a perturbation factor $P_F$ ($P_F$=4) in this example,
the growing process 68 is applied resulting in a new larger blob,
the threshold $L_T$ is adjusted by subtracting the perturbation factor $P_F$, and
the growing process 68 is applied resulting in a new smaller blob, A logical EXOR function is then computed between the new larger and smaller blobs: i.e. each pixel in the smaller blob is EXORed with a respective pixel in the same position in the larger blob. Outer pixels of the larger blob for which there are no like-located pixels in the small blob are treated as being EXORed with a different pixel value. The EXOR function yields a 1 for a pair of pixels of different value and a 0 for a pair of pixels of the same value. Its results provide an EXOR image with each EXOR value located as a pixel in the same position as the blob pixels giving rise to it. The number of pixels equal to 1 in the EXOR image is then counted and this number is the perturbed difference.

The Hue difference is obtained for each blob as follows: the average colour of the median filtered image pixels located in the same positions as the pixels of the blob is computed. This average colour and the background pixel colour obtained earlier are then converted from red/green/blue (RGB) to a different image space hue/saturation/value (HSV). The RGB to HSV transformation is described by K. Jack in 'Video Demystified', $2^{nd}$ ed., HighText Publications, San Diego, 1996. In this example the V and S components are not required. H is calculated for the average colour of each blob and the background pixel colour as follows:

Let M=maximum of (R,G,B)  (17)

Let m=minimum of (R,G,B)  (18)

Then new$r=(M-R)/(M-m)$  (19)

new$g=(M-G)/(M-m)$  (20)

new$b=(M-B)/(M-m)$  (21)

Hue (H) then given by:

If $R$ equals $M$ then $H=60(\text{new}b-\text{new}g)$  (22)

If $G$ equals $M$ then $H=60(2+\text{new}r-\text{new}b)$  (23)

If $B$ equals $M$ then $H=60(4+\text{new}g-\text{new}r)$  (24)

If $H$ greater than or equal 360 then $H=H-360$  (25)

If $H$ less than 0 then $H=H+360$  (26)

The difference between the H values of the average colour of the median filtered image pixels in the blob and the background pixel is then calculated for each blob and becomes designated as the Hue difference for that blob.

If a blob's parameters satisfy all the conditions in the table immediately below then the blob is accepted for further processing, otherwise it is rejected (deleted) by setting all its pixels to 0.

| Parameters for Accepted Blobs |
| --- |
| 355 pixels < Area < 1700 pixels |
| 0.17 < Compactness < 0.77 |
| Ratio of width/height < 2.7 |
| Luminance percentage < 44 |
| Perturbed difference < Area × 23/100 |
| Hue difference > 0 |

In the present example, the Hue difference will virtually always be true (due to the zero threshold in the table immediately above). However in some circumstances it may be desirable to have a non-zero threshold. Luminance percentage, perturbed difference and Hue difference are not essential, and can be omitted from the thresholds in the table above governing further processing or otherwise.

At 72 a two quicksorts (as previously defined) are applied to the blobs to sort them into two lists, one of blobs in ascending order of blob area and the other of blobs in ascending order of blob luminance in the median filtered image. The blobs in the two lists are now referred to in accordance with groupings that they mark the end of: i.e. a blob is referred to as the "darkest X % blob" to indicate that it together with blobs (if any) of lower luminance than it are X % of the total number of blobs. Similarly, a blob is referred to as the "largest Y % blob" to indicate that it together with blobs (if any) of greater area than it are Y % of the total number of blobs.

A blob of median area (the "median blob", central in the area list) is now identified. If there is an even number of blobs in the area list, the average area of the two central blobs is taken as the median area. Also at 72, unwanted blobs are eliminated to leave those assessed as corresponding to mitotic figures as follows: if more than A blobs are present and the largest blob is more than B percent of the area of the median blob, we retain each of the largest C blobs which has a luminance not greater than that of the darkest D percent blob. Otherwise, if the largest blob is not more than B percent of the area of the median blob, retain each of the darkest E blobs which has an area less than or equal the largest F percent blob. In this example, values for A, B, C, D, E and F are A=2 blobs, B=200 percent, C=3 blobs, D=30 percent, E=2 blobs, F=80 percent. The process 72 is computed as follows:

If the number of blobs is less than or equal to A then accept each blob as being a mitotic figure, the mitotic figure count is A and processing the current image terminates.

Otherwise, if the number of blobs is greater than A:
  obtain area of largest blob,
  obtain area of median blob,
  if the largest blob area is more than B percent of the median blob area, then:
    obtain the luminance of the darkest D percent blob—if there is no blob at a
    D percent position take the luminance of a blob which is both darker and nearest to a notional D percent blob position in the luminance list,
    for each of the largest C blobs,
      if blob luminance is less than or equal to the darkest D percent blob,
        accept the blob as being a detected mitotic figure,
        increase a count of mitotic figures by 1, and
        repeat for remainder of largest C blobs until none remain unassessed and output count of mitotic figures.
  Otherwise, if largest blob area is not more than B percent of median blob area,
    obtain the area of the largest F percent blob—if there is no blob at an F percent position take the area of a blob which is nearest (in area) to a notional F percent blob position in the area list,
  For each of the darkest E blobs
    if blob area is less than or equal to area of the largest F percent blob,
      accept the blob as being a detected mitotic figure, and
      increase a count of mitotic figures (initially 0) by 1,
      repeat for remainder of the largest E blobs until none remain unassessed and output count of mitotic figures.

The criterion number of blobs is not greater than A may be the only one used if desired, the mitotic count being taken as zero if this is not satisfied. The "otherwise" criterion, i.e. number of blobs greater than A and subsequent criteria, provide a further option.

As previously mentioned, the process 20 is carried out for a total of ten images or tiles: this repetition is to increase the likelihood of observing mitotic activity. The mitotic counts for the ten images are then added together to provide a sum which is converted to a mitotic activity grading as will be described later.

Referring now to FIG. 6, there is shown a flow diagram of an alternative mitotic feature detection process 24 which is carried out for each of the ten digitised images mentioned above. Although it is possible to use the whole image, at 120 the digitised image (hereinafter the "input image") is for convenience separated into overlapping windows of size 128×128 pixels. The windows overlap with 64 pixels in both horizontal and vertical directions. Thus, each window overlaps half of its preceding window above and to the left (if available). In each window Principal Component Analysis (PCA, Karhunen-Loeve Transform) is applied. PCA is a standard mathematical technique described by Jollie I. T., 'Principal Component Analysis', Springer series in statistics, Springer Verlag, 1986. It is also described by Jackson J. E., 'A User Guide to Principal Components' pp 1-25, John Wiley & Sons, 1991. PCA is a technique for transforming a set of (possibly correlated) variables into a smaller number of uncorrelated variables called principal components. The first principal component accounts for as much of the variability in the set of variables as possible as compared to the other components: because of this it can be superior to taking a red, green or blue image plane or an average thereof, which are also options at this step. PCA involves obtaining a covariance matrix of the set of variables and solving for its eigenvalues and eigenvectors. The covariance matrix is calculated using the formula $$C_{i,j} = \frac{\sum_{k=1}^{N}(x_k - \mu_x)(y_k - \mu_y)}{N-1} \quad (27)$$

where $C_{i,j}$ is the covariance of variable i with variable j, $x_k$ and $y_k$ are the ith and jth feature values of the kth object, $\mu_x$ is the mean of all N values of $x_k$, $\mu_y$ is the mean of all N values of $y_k$. The covariance matrix is 3×3 and PCA yields three eigenvectors: the eigenvectors are treated as a 3×3 matrix, which is used to multiply the transpose of the N×3 image matrix to produce a product matrix. The product matrix has an N×1 first column which is the first principal component, which may be considered as the most important component. It is the component with the maximum eigenvalue, and it provides a greyscale sub-image (one pixel value for each of N pixels) with a maximum range of information compared to equivalents associated with other components. PCA is carried out for each of the overlapping windows defined above and each provides a respective first principal component and greyscale sub-image of size 128×128 pixels.

At 122, each sub-image resulting from 120 is converted to a corresponding binary sub-image by applying a thresholding method referred to as "Otsu". Otsu is a standard thresholding technique published by Otsu N., 'A thresholding selection method from grey level-histograms', IEEE Trans Systems, Man & Cybernetics, vol. 9, 1979, pp 62-66. The Otsu threshold selection method aims to minimise for two classes a ratio of between-class variance to within-class variance: i.e. the higher the variance between classes the better the separation. In the present example the two classes are a below-threshold class (pixel value 0) and an above-threshold class (pixel value 1), so by applying Otsu thresholding the greyscale sub-image is converted into a binary sub-image containing a set of blobs.

At 124 all blobs (objects) that touch or intersect sub-image boundaries are removed. Thus, if at any pixel a blob meets a border it is removed by setting its pixels to a background pixel value. This is because such boundaries give blobs meeting them artificial straight edges which can give misleading results later. Because of sub-image overlap, a blob which appears partly in one image may appear wholly in another sub-image. This step 124 only arises from the use of sub-images.

At 126 the outputs from 124 are inverted and connected component labelling (CCL, as described earlier) is applied in order to enable any holes in the blobs to be removed. This is not essential, but it provides spatial filtering which improves results somewhat. Because of the inversion, areas of pixel value 1 labelled by CCL labelling will be background pixels and holes within blobs. Holes, i.e. all labelled areas other than background pixels, are removed (filled in) by setting pixels of holes in each blob to the value of the blob's other pixels.

At 128 the outputs from 126 are inverted once more and CCL is applied: after this inversion, the labelled areas are the blobs within the sub-image filled at 126. CCL also yields blob centre positions used later. Any blobs smaller than a minimum area threshold of 400 pixels are rejected, i.e. set to an image background value, in accordance with the table immediately below. This is another desirable but not essential spatial filtering step.

| | |
|---|---|
| Blob size < min area (400 pixels) | Reject blob |
| Otherwise | Accept for further processing into set of labelled blobs |

At 130 multiple sub-images output at 128 are reassembled into a new binary image which is the same size as the original before decomposition at 120; the new binary image has undergone filtering and now contains only blobs that are of interest for subsequent mitosis processing. Image preprocessing terminates with step 130: the set of blobs remaining has been cleared both of unwanted small blobs and of holes within blobs. Image preprocessing using steps 120-130 is advantageous because it does not significantly affect shapes of blob perimeters, which is important for mitosis analysis. Results from whichever of the mitosis cueing processes 16 and 18 has been used are introduced in this step 130: i.e. a blob is accepted or rejected according to whether or not there is a blob in the mitosis cued image in substantially the same position (this could be implemented lo using a logical AND operation). It is not essential to use a process 16 or 18 here but it is useful to reduce processing burden.

At 132 Principal Component Analysis (PCA, as previously described) is applied to the entire input (RGB) image. As before, a, red, green or blue image plane or an average thereof could be used, but PCA is preferred. PCA yields a first component which is a greyscale image with a better information range than those of other components. A feature extraction procedure 134 is applied to a local window of 51×51 pixels centered on the centres of each of the blobs identified in pre-processing at 130 and appearing in the greyscale image. The procedure 134 determines an average cross-section (profile) for that respective region of the greyscale image that corresponds to each blob: for the purposes of this calculation each greyscale value used is normalised to lie in the range 0 to 1 by dividing it by 255. A respective series of profiles of each blob is taken using a line fifty-one pixels long extending across the respective greyscale image region corresponding to that blob and centered on the blob centre: this gives fifty-one pixel values or histogram points per profile, and profiles are taken at nine different angular orientations at 20 degree intervals: the respective mean of the nine profiles of each blob is then calculated.

A respective histogram of each mean profile is then obtained and quantised to just five intervals or bins 1 to 5 as follows, (1) $0.1 \leq profile < 0.2$, (2) $0.2 \leq profile < 0.4$, (3) $0.4 \leq profile < 0.6$, (4) $0.6 \leq profile < 0.8$, and (5) $0.8 \leq profile \leq 1.0$. The bins have centres at 0.1, 0.3, 0.5, 0.7 and 0.9 respectively. Each bin contains the number of pixels in the mean profile having its respective intensity value. Bin 1 corresponds to a darkest group of image intensity values, i.e. low greyscale values of the kind one would associate with images of mitotic figures; mitotic figures are normally dark using conventional staining techniques so relatively darker degrees of grey level are of more interest bins 2 to 4 correspond to progressively brighter values and bin 5 to the brightest of the five values. These are relative though because the profiles all come from relatively dark image regions. An approximate mean profile is represented by five values. Each set of five values characterises a blob now treated as indicating an actual cell. The minimum value of each mean profile is recorded as the variable 'minprofile'.

At 136 the contents of bins 1, 2 and 4 are used to determine if a current cell that corresponds to a current blob is mitotic or not. Specifically, the following criteria are applied for each blob, where "bin (n)" means the contents of the nth bin and n=1, 2 or 4:

If bin (1)>7.6, then:
current cell is mitotic.
Otherwise, if bin (1)≤7.6, then
if bin (2)>25.5 and bin (4)>0 and minprofile<0.15, then:
current cell is mitotic
otherwise, i.e. if bin (2)≤25.5 and/or bin (4)≤0 and/or minprofile≥0.15) then
current cell is not mitotic The first criterion—bin (1)>7.6—may if desired be the only one used to determine whether a cell is mitotic. The "otherwise" criterion—bin (1)≤7.6—is optional.

Each alternative mitotic feature detection technique 20 and 24 produces measurements derived from ten images. Each mitotic feature detection technique is applied to ten images or tiles as has been said: the mitotic figures are counted for each image and the counts are added together to provide a total for the ten images. The mitotic figure count for a technique is low, medium or high with points 1, 2 or 3 according to whether it is 0 to 5, 6 to 10 or 11 or more respectively as shown in the table below.

| Measurement: Number of Mitotic figures in Ten Images | Meaning | Points |
|---|---|---|
| 0-5 | Low | 1 |
| 6-10 | Moderate | 2 |
| ≥11 | High | 3 |

The measurement of mitosis may be combined with others obtained for pleomorphism and tubules by different methods to derive an overall grading referred to in medicine as a "Bloom and Richardson grading": it is used by clinicians as a measure of cancer status.

The examples given in the foregoing description for calculating intermediate quantities and results can clearly be evaluated by an appropriate computer program recorded on a carrier medium and running on a conventional computer system. Examples of program steps haven been given. Such a program is straightforward for a skilled programmer to implement without requiring invention, because the procedures are well known. Such a program and system will therefore not be described further.

The invention claimed is:

1. A method of measurement of mitotic activity from histopathological specimen image data, the method comprising the steps of:
   a) identifying pixels in the image data having luminances associated with mitotic figures;
   b) selecting from among the identified pixels a reference pixel which is sufficiently close in position and luminance to another identified pixel to provide a reference colour;
   c) locating pixels in the image data with luminances sufficiently close to that of the reference colour to indicate potentially mitotic figures;
   d) incrementing image regions corresponding to potentially mitotic figures from the located pixels by adding pixels thereto, potential increments to image regions being implemented or rejected by according to whether or not their luminances are sufficiently close to respective image region luminances and sufficiently far from an image data background luminance;
   e) selecting grown image regions on the basis of thresholds for image region area, compactness and width/height ratio; and
   f) counting selected grown image regions as actually indicating mitotic figures on the basis of thresholds for number of such regions;
   wherein the method is implemented by a processor.

2. A method according to claim 1 wherein the step of selecting grown image regions also involves thresholds for ratio of image region luminance to background luminance and area difference between areas derived by growing each image region with multiple thresholds.

3. A method according to claim 2 wherein the thresholds for image region area, compactness, width/height ratio, luminance and area difference are: 355 pixels<area<1700 pixels, 0.17<compactness<0.77, width/height ratio<2.7, luminance percentage<44%, area difference<23 area/100.

4. A method according to claim 1 wherein the step of counting selected grown image regions as actually indicating mitotic figures also involves thresholds for region area and luminance.

5. A method according to claim 1 wherein successive potential increments to image regions are individual pixels each of which is an immediate row or column neighbor of an existing image region pixel.

6. A method according to claim 1 wherein step b) is implemented with a reference pixel having a luminance differing by less than 8% compared to another identified pixel distant from it by not more than two percent of a smaller of two image dimensions.

7. A method according to claim 1 wherein step a) includes white balancing and median filtering the image data prior to identifying pixels having luminances corresponding to mitotic figures.

8. A method according to claim 1 wherein in step c) pixels are cued for acceptance or rejection as regards indicating mitotic figures by:
   a) thresholding colour image data to remove pixels lacking intensities associated with mitotic figure imagery,
   b) removal pixels not present in all colors, and c) thresholding image region areas to remove those too small and too large to be potential mitotic figures.

9. A method according to claim 1 wherein in step c) pixels are cued for acceptance or rejection as regards indicating mitotic figures by:
   a) segmenting to identify pixels with intensities associated with mitotic figure imagery,
   b) thresholding image region areas to remove those too small and too large to be potential mitotic figures,
   c) cluster analysis to determine whether or not a pixel's image region is in a sufficiently large cluster, and
   d) necrotic and hairy edge filtering.

10. A method of measuring mitotic activity from histopathological specimen color image data, the method having the steps of:
   a) staining a histopathological specimen with a staining agent to color and delineate tissue and cellular structure appropriately for assessment of mitotic activity,
   b) obtaining color image data from the staining of the stained histopathological specimen,
   Wherein the steps c-g are implemented by a processor;
   c) measuring an intensity profile of an image region in the color image data, the image region corresponding to a potentially mitotic figure,
   d) counting the image region as indicating a mitotic figure if its intensity profile has a non-zero number of pixels with intensity associated with mitotic figure imagery, and that pixel number is greater than a prearranged threshold value,
   e) if one or more other image regions corresponding to potentially mitotic figures are available in the specimen image, repeating steps c) and d) for such region or regions,
   f) repeating steps c), d) and e) for additional histopathological specimen image data in order to obtain mitotic figure counts for a plurality of specimen images, and
   g) summing the mitotic figure counts obtained in steps c) to f) to provide an indication of degree of mitotic activity.

11. A method of measuring mitotic activity from histopathological specimen image data, the method having the steps of:
   a) measuring an intensity profile of an image region corresponding to a potentially mitotic figure, and
   b) counting the image region as indicating a mitotic figure if its profile has a first value not greater than the prearranged threshold at a position in the profile having intensity associated with mitotic figure imagery, a second value greater than a prearranged second threshold, a third value greater than a prearranged third threshold, and a minimum value less than a prearranged fourth threshold;
   wherein the method is implemented by a processor.

12. A method according to claim 11 wherein the first value is at one end of the profile, the first and second values adjoin one another in the profile and the third value does not adjoin the second value.

13. A method according to claim 11 wherein the image data comprise a first Principal Component obtained by Principal Component Analysis (PCA) of colored image data.

14. A method according to claim 11 wherein step a) includes preprocessing image data by:
   i) decomposing the image data into overlapping sub-images,
   ii) applying PCA to the sub-images to derive a first Principal Component image,
   iii) thresholding the first Principal Component image to produce a binary image of blobs and background
   iv) rejecting blobs adjacent to or intersecting sub-image boundaries,
   v) filling holes in blobs,
   vi) rejecting blobs too small to correspond to potential mitotic figures, and
   vii) reassembling the sub-images into a single image for image region profile measurement as aforesaid in step a).

15. A method according to claim 14 wherein after step g) pixels are cued for acceptance or rejection as regards indicating mitotic figures by:
   a) thresholding colour image data to remove pixels lacking intensities associated with mitotic figure imagery,
   b) removal pixels not present in all colors, and
   c) thresholding image region areas to remove those too small and too large to be potential mitotic figures.

16. A method according to claim 14 wherein after step g) pixels are cued for acceptance or rejection as regards indicating mitotic figures by:
   a) segmenting to identify pixels with intensities associated with mitotic figure imagery,
   b) thresholding image region areas to remove those too small and too large to be potential mitotic figures,
   c) cluster analysis to determine whether or not a pixel's image region is in a sufficiently large cluster, and
   d) necrotic and hairy edge filtering.

17. Computer apparatus for measuring mitotic activity from histopathological specimen image data, the apparatus being programmed to execute the steps of:
   a) identifying pixels in the image data having luminances associated with mitotic figures;
   b) selecting from among the identified pixels a reference pixel which is sufficiently close in position and luminance to another identified pixel to provide a reference colour;
   c) locating pixels in the image data with luminances sufficiently close to that of the reference colour to indicate potentially mitotic figures;
   d) incrementing image regions corresponding to potentially mitotic figures from the located pixels by adding pixels thereto, potential increments to image regions being implemented or rejected by according to whether or not their luminances are sufficiently close to respective image region luminances and sufficiently far from an image data background luminance;
   e) selecting grown image regions on the basis of thresholds for image region area, compactness and width/height ratio; and
   f) counting selected grown image regions as actually indicating mitotic figures on the basis of thresholds for number of such regions.

18. Computer apparatus according to claim 17 programmed to execute the step of selecting grown image regions by also using thresholds for ratio of image region luminance to background luminance and area difference between areas derived by growing each image region with multiple thresholds.

19. Computer apparatus according to claim 18 wherein the thresholds for image region area, compactness, width/height ratio, luminance and area difference are: 355 pixels<area<1700 pixels, 0.17<compactness<0.77, width/height ratio<2.7, luminance percentage<44%, area difference<23 area/100.

20. Computer apparatus according to claim 17 programmed to execute the step of counting selected grown image regions as actually indicating mitotic figures by also using thresholds for region area and luminance.

21. Computer apparatus according to claim 17 wherein successive potential increments to image regions are individual pixels each of which is an immediate row or column neighbor of an existing image region pixel.

22. Computer apparatus according to claim 17 programmed to execute step b) with a reference pixel having a luminance differing by less than 8% compared to another identified pixel distant from it by not more than two percent of a smaller of two image dimensions.

23. Computer apparatus for measuring mitotic activity from histopathological specimen color image data obtained from a histopathological specimen stained with a staining agent to color and delineate tissue and cellular structure appropriately for assessment of mitotic activity, the apparatus being programmed to execute the steps of:
   a) measuring an intensity profile of an image region in the color image data, the image region corresponding to a potentially mitotic figure,
   b) counting the image region as indicating a mitotic figure if its intensity profile has a non-zero number of pixels with intensity associated with mitotic figure imagery, and that pixel number is greater than a prearranged threshold value,
   c) if one or more other image regions corresponding to potentially mitotic figures are available in the specimen image, repeating steps a) and b) for such region or regions,
   d) repeating steps a), b) and c) for additional histopathological specimen image data in order to obtain mitotic figure counts for a plurality of specimen images, and
   e) summing the mitotic figure counts obtained in steps a) to d) to provide an indication of degree of mitotic activity.

24. Computer apparatus for measuring mitotic activity from histopathological specimen image data, the apparatus being programmed to execute the steps of:
   a) measuring an intensity profile of an image region corresponding to a potentially mitotic figure, and
   b) counting an image region as indicating a mitotic figure if its profile has a first value not greater than the prearranged threshold at a position in the profile having intensity associated with mitotic figure imagery, a second value greater than a prearranged second threshold, a third value greater than a prearranged third threshold, and a minimum value less than a prearranged fourth threshold.

25. Apparatus according to claim 24 wherein the first value is at one end of the profile, the first and second values adjoin one another in the profile and the third value does not adjoin the second value.

26. Apparatus according to claim 24 wherein the image data comprise a first Principal Component obtained by Principal Component Analysis (PCA) of colored image data.

27. A computer software product comprising a computer readable medium encoded with computer readable instructions and for use in measuring mitotic activity from histopathological specimen image data, the computer readable instructions being for controlling computer apparatus to implement the steps of:
   a) identifying pixels in the image data having luminances associated with mitotic figures;
   b) selecting from among the identified pixels a reference pixel which is sufficiently close in position and luminance to another identified pixel to provide a reference colour;
   c) locating pixels in the image data with luminances sufficiently close to that of the reference colour to indicate potentially mitotic figures;
   d) incrementing image regions corresponding to potentially mitotic figures from the located pixels by adding pixels thereto, potential increments to image regions being implemented or rejected by according to whether or not their luminances are sufficiently close to respective image region luminances and sufficiently far from an image data background luminance;
   e) selecting grown image regions on the basis of thresholds for image region area, compactness and width/height ratio; and
   f) counting selected grown image regions as actually indicating mitotic figures on the basis of thresholds for number of such regions.

28. A computer software product according to claim 27 wherein the computer readable instructions provide for implementing the step of selecting grown image regions by also using thresholds for ratio of image region luminance to background luminance and area difference between areas derived by growing each image region with multiple thresholds.

29. A computer software product according to claim 28 wherein the thresholds for image region area, compactness, width/height ratio, luminance and area difference are: 355 pixels<area<1700 pixels, 0.17<compactness<0.77, width/height ratio<2.7, luminance percentage<44%, area difference<23 area/100.

30. A computer software product according to claim 27 wherein the computer readable instructions to provide for implementing the step of counting selected grown image regions as actually indicating mitotic figures using also thresholds for region area and luminance.

31. A computer software product comprising a computer readable medium encoded with computer readable instructions for use in measuring mitotic activity from histopathological specimen color image data obtained from a histopathological specimen stained with a staining agent to color and delineate tissue and cellular structure appropriately for assessment of mitotic activity, the computer readable instructions being for controlling computer apparatus to implement the steps of:
   a) measuring an intensity profile of an image region in the color image data, the image region corresponding to a potentially mitotic figure,
   b) counting the image region as indicating a mitotic figure if its intensity profile has a non-zero number of pixels with intensity associated with mitotic figure imagery, and that pixel number is greater than a prearranged threshold value,
   c) if one or more other image regions corresponding to potentially mitotic figures are available in the specimen image, repeating steps a) and b) for such region or regions,
   d) repeating steps a), b) and c) for additional histopathological specimen image data in order to obtain mitotic figure counts for a plurality of specimen images, and
   e) summing the mitotic figure counts obtained in steps a) to d) to provide an indication of degree of mitotic activity.

32. A computer software product comprising a computer readable medium encoded with computer readable instructions and for use in measuring mitotic activity from histopathological specimen image data, the computer readable instructions being for controlling computer apparatus to implement the steps of:
   a) measuring an intensity profile of an image region corresponding to a potentially mitotic figure, and
   b) counting the image region as indicating a mitotic figure if its profile has a first value not greater than the prearranged threshold at a position in the profile having intensity associated with mitotic figure imagery, a second value greater than a prearranged second threshold, a third value greater than a prearranged third threshold, and a minimum value less than a prearranged fourth threshold.

33. A computer software product according to claim 32 wherein the first value is at one end of the profile, the first and second values adjoin one another in the profile and the third value does not adjoin the second value.

34. A computer software product according to claim 32 wherein the computer readable instructions provide for step a) to include preprocessing image data by:
   i) decomposing the image data into overlapping sub-images,
   ii) applying PCA to the sub-images to derive a first Principal Component image,
   iii) thresholding the first Principal Component image to produce a binary image of blobs and background
   iv) rejecting blobs adjacent to or intersecting sub-image boundaries,
   v) filling holes in blobs,
   vi) rejecting blobs too small to correspond to potential mitotic figures, and
   vii) reassembling the sub-images into a single image for image region profile measurement as aforesaid in step a).

* * * * *

UNITED STATES PATENT AND TRADEMARK OFFICE
CERTIFICATE OF CORRECTION

PATENT NO. : 7,577,280 B2
APPLICATION NO. : 10/535140
DATED : August 18, 2009
INVENTOR(S) : Guittet et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 937 days.

Signed and Sealed this

Seventh Day of September, 2010

David J. Kappos
*Director of the United States Patent and Trademark Office*